United States Patent [19]

Pera

[11] Patent Number: 4,906,488
[45] Date of Patent: Mar. 6, 1990

[54] MODIFICATION OF PERMEANT

[75] Inventor: Ivo E. Pera, Pisa, Italy

[73] Assignee: Arcade, Inc., Chattanooga, Tenn.

[21] Appl. No.: 68,275

[22] Filed: Jul. 1, 1987

Related U.S. Application Data

[63] Continuation-in-part of Ser. No. 44,677, May 1, 1987, and a continuation-in-part of Ser. No. 55,574, May 29, 1987, abandoned.

[51] Int. Cl.$^4$ .......................... A23L 1/04; A61K 7/46
[52] U.S. Cl. ................................. 426/573; 252/315.1;
252/315.3; 264/4.1; 264/4.7; 424/76.3;
424/419; 424/486; 426/533; 426/534; 426/650;
426/651; 512/4; 514/944; 514/965
[58] Field of Search ..................... 252/315.1; 424/419,
424/486; 514/944, 965; 426/573; 512/4

[56] References Cited

U.S. PATENT DOCUMENTS 4,058,491 11/1977 Steckler .......................... 514/944 X
4,178,361 12/1979 Cohen et al. .................... 424/486 X
4,291,015 9/1981 Keith et al. .......................... 424/486

Primary Examiner—Richard D. Lovering
Attorney, Agent, or Firm—Joseph H. Beumer

[57] ABSTRACT

Forming a solution (preferably a true or complete solution) of mer in any permeant, reacting mer in presence of permeant substantially without rearrangement of the liquid system into separate phases and substantially without encapsulation (defined as any form of entrapment by polymeric solidification, including microencapsulation) and recovering a liquid product useful in formulating slow-release products.

12 Claims, No Drawings

MODIFICATION OF PERMEANT

CROSS REFERENCE TO RELATED APPLICATIONS

This application is a continuation-in-part of two prior copending patent applications filed in the U.S. Patent and Trademark Office and entitled Permeant Modification, the first being U.S. patent application Ser. No. 044,677, filed May 1, 1987 and the second being Ser. No. 055,574, filed May 29, 1987 and now abandoned. The disclosures of said applications are incorporated herein by reference.

TECHNICAL FIELD

The present invention relates to the modification of permeants by reaction of mers in the presence of permeants to form products of signifcantly increased molecular weight. Preferably, the invention relates to reactions of mers in the presence of permeants in liquid systems to form liquid products of substantially increased molecular weight, in which products the permeants are distributed for performing their characteristic functions in a host medium outside the reaction product.

BACKGROUND OF THE INVENTION

Permeants are any of a wide variety of materials which perform useful functions by distributing themselves via physical and/or chemical transport mechanisms, such as diffusion, evaporation or the like, throughout a host medium, such as a gas, liquid, solid or combination thereof. Some examples of permeant materials which find wide use in industrial, commercial, domestic and medical applications are perfumes, disinfectants, foods, pharmaceuticals, flavors, insecticides, insect repellents, cleansing and cleaning materials, preservatives, emollients, exipients, stabilizers, dyes, diluents, lotions, inhalants, fungicides, air fresheners, anti-static agents, corrosion inhibitors, fertilizers, enzymes, poisons and lures.

It is well known to entrap permeants in bulk polymers or microcapsules to attain controlled/sustained release of the permeant. Examples may be found in U.S. Pat. Nos. 2,007,721, 2,467,583, 3,041,289, 3,047,431, 3,140,184, 3,400,093, 3,528,819, 3,551,556, 3,577,512, 3,618,604, 3,626,940, 3,630,200, 3,641,237, 3,660,071, 3,689,634, 3,761,286, 3,857,964, 3,868,447, 3,872,023, 3,881,026, 3,886,125, 3,939,099, 3,941,858, 4,003,846, 4,009,684, 4,010,038, 4,011,311, 4,066,387, 4,089,800, 4,110,261, 4,125,370, 4,145,184, 4,206,301, 4,226,944, 4,230,687, 4,257,176, 4,269,729, 4,275,194, 4,277,364, 4,309,509, 4,310,397, 4,321,252, 4,328,119, 4,339,356, 4,344,857, 4,344,857, 4,350,774, 4,356,115, 4,380,552, 4,380,626, 4,381,066, 4,382,813, 4,386,108, 4,386,193, 4,391,717, 4,401,456, 4,401,456, 4,407,795, 4,409,201, 4,413,843, 4,423,091, 4,423,099, 4,434,086, 4,435,383, 4,439,488, 4,439,488, 4,446,032, 4,456,587, 4,462,880, 4,515,909, 4,521,541, 4,522,953, 4,524,068, 4,525,520, 4,540,721, 4,542,162, 4,543,367, 4,552,693, 4,555,438, 4,555,504, 4,557,929, 4,565,807, 4,569,852, 4,580,581, 4,582,635, 4,587,129, 4,598,070, 4,603,123, 4,618,629, 4,629,621, 4,634,614, 4,649,082, 4,650,898 and 4,663,316.

At present, one of the commercially popular applications of microencapsulation technology is encapsulation of fragrances to form microcapsules that are distributed on a paper substrate for use as advertising matter in the form of magazine inserts, blotters and the like. A number of problems have been encountered in this field, including premature/excessive release of the fragrance or portions thereof. Also, this technology could achieve wider commerical utilization if it could be performed more economically with more effective and controllable entrapment. Optionally, the technology could achieve wider utilization if it could be successfully applied to water-soluble or hydrophilic water-insoluble permeants which heretofore have been at least difficult if not impossible to encapsulate successfully. This invention, among other things, provides solutions to these needs.

SUMMARY OF THE INVENTION

The present invention is a method of modifying a permeant comprising forming a liquid system including a solution of a mer with a permeant, reacting the mer in the presence of the permeant in a portion of the liquid system which contains substantial amounts of both mer and permeant for significantly increasing the molecular weight of the mer under conditions which substantially preserve at least one useful permeant function of the permeant, continuing the reaction under such conditions to a sufficient extent for substantially reducing the diffusion rate, volatility, flammability, toxicity or susceptibility to oxidation or other form of environmental attack upon the permeant, and recovering a product of reaction of said mer substantially without rearrangement of the liquid system into separate phases and substantially without encapsulation of the permeant and having a consistency ranging from a liquid to a non-self-supporting soft gel, from which product the permeant may escape for performing its permeant function in or on a host medium outside the reaction product. Products produced according to the foregoing method are also part of the invention.

Moreover, the invention includes certain further improvements, all of which can be used singly or in any operative combination in or with the above-described methods and products of the present invention. These further improvements are discussed below under the heading "Description of Various and Preferred Embodiments". Among them are a number of particularly preferred embodiments of the invention, including recovery of the product of reaction as a liquid.

In the practice of the invention the permeant may include an olfactant, flavor, pesticide, repellant, cleansing or cleaning material, preservative, emollient, excipient, stabilizer, dye, diluent, lotion, anti-static agent, corrosion inhibitor, fertilizer, enzyme or lure.

Among the applicable mers are polyvinylpyrrolidone, a cyclodextrin, algin, chitin or a monomer or derivative of any of them. Polyvinylpyrrolidone is the preferred mer, especially with a molecular weight in the range of about 5,000 to about 200,000 and more preferably about 7,000 to about 160,000. A preferred cyclodextrin is beta-cyclodextrin having a molecular weight of at least about 1,000. Where the mer includes algin, the preferred reaction product includes an alginate. Chitosan is a preferred chitin derivative.

Valuable products can be produced by applying the reaction product of the method to a substrate, and the invention therefore includes the corresponding products.

The invention provides the opportunity for obtaining for one or more of the following advantages with respect to the performance of the permeant in its end-use application(s), including, for example, reduction of diffusion rate, volatility, flammability, toxicity, and oxidation or other environmental attack. With certain permeants, the invention provides opportunities for providing or enhancing one or more of the following properties in the resultant product, including longevity of the action of the permeant, gloss, moldability, resiliency and miscibility with certain liquids. Because certain permeants are not readily convertible to gel-form by other means, the invention opens up new applications for certain of these permeants.

A particularly important advantage of the invention is that it can convert perfumes and other fragrances to slower-diffusing liquid forms or to forms that are at least pseudo-solid while preserving the integrity of delicate odors, including their top notes, and with uniformity from batch to batch. Since certain embodiments of the invention can be performed at room temperature and do not require major alterations of the pH in the liquid system, they can, where necessary or desirable, be readily applied to a wide variety of temperature- and pH- sensitive permeants.

DESCRIPTION OF VARIOUS AND PREFERRED EMBODIMENTS

The present invention can be embodied in a wide variety of forms, some of which will be described below. According to the invention a reaction is conducted in a liquid system which comprises, or consists essentially of, or consists of, a mer and a permeant and other liquid or non-liquid ingredients useful in forming certain reaction products. Specific examples of the process materials and descriptions of how to form the liquid system, conduct the reaction, recover the resultant reaction products and apply them industrially are set forth below.

Permeant

As indicated above, permeants are materials which perform useful functions by distributing themselves via physical and/or chemical transport mechanisms, such as diffusion, evaporation or the like, throughout a host medium, such as a gas, liquid, solid or combination thereof. The desired materials have utility in performing a permeant function in a host medium outside the reaction product. Thus, instead of treating the reaction product, the permeant is transported into and treats or otherwise acts upon something in an adjoining or surrounding host medium, including the host medium itself.

Preferred categories of permeants include olfactants, flavors, medicaments and pesticides.

Among the useful olfactants are natural fragrances, synthetic fragrances, synthetic essential oils and natural essential oils.

Examples of the synthetic fragrances include terpenic hydrocarbons, esters, ethers, alcohols, aldehydes, phenols, ketones, acetals, oximes and mixtures thereof.

Examples of the terpenic hydrocarbons include lime terpene, lemon terpene and limonen dimer.

Examples of the esters include γ-undecalactone, ethyl methyl phenyl glycidate, allyl caproate, amyl salicylate, amyl benzoate, amyl acetate, benzyl acetate, benzyl benzoate, benzyl salicylate, benzyl propionate, butyl acetate, benzyl butyrate, benzyl phenylacetate, cedryl acetate, citronellyl acetate, citronellyl formate, p-cresyl acetate, 2-t-pentyl-cyclohexyl acetate, cyclohexyl acetate, cis-3-hexenyl acetate, cis-3-hexenyl salicylate, dimethylbenzyl acetate, diethyl phthalate, δ-deca-lactone dibutyl phthalate, ethyl butyrate, ethyl acetate, ethyl benzoate, fenchyl acetate, geranyl acetate, γ-dodecalatone, methyl dihydrojasmonate, isobornyl acetate, β-isopropoxyethyl salicylate, linalyl acetate, methyl benzoate, o-t-butylcylohexyl acetate, methyl salicylate, ethylene brassylate, ethylene dodecanoate, methyl phenyl acetate, phenylethyl isobutyrate, phenylethylphenyl acetate, phenylethyl acetate, methyl phenyl carbinyl acetate, 3,5,5-trimethylhexyl acetate, terpinyl acetate, triethyl citrate, p-t-butylcyclohexyl acetate and vetiver acetate.

Examples of the ethers include p-cresyl methyl ether, diphenyl ether, 1,3,4,6,7,8-hexahydro-4,6,7,8,8-hexamethyl cyclopenta-β-2-benzopyran and phenyl isoamyl ether.

Examples of the alcohols include n-octyl alcohol, n-nonyl alcohol, β-phenylethyldimethyl carbinol, dimethyl benzyl carbinol, carbitol dihydromyrcenol, dimethyl octanol, hexylene glycol linalool, leaf alcohol, nerol, phenoxyethanol, γ-phenyl-propyl alcohol, β-phenylethyl alcohol, methylphenyl carbinol, terpineol, tetrahydroalloocimenol, tetrahydrolinalool and 9-decen-1-ol.

Examples of the aldehydes include n-nonyl aldehyde, undecylene aldehyde, methylnonyl acetaldehyde, anisaldehyde, benzaldehyde, cyclamenaldehyde, 2-hexylhexanal, ahexylcinnamic alehyde, phenyl acetaldehyde, 4-(4-hydroxy-4-methylpentyl)-3-cyclohexene-1-carboxyaldehyde, p-t-butyl-a-methylhydrocinnamic aldehyde, hydroxycitronellal, α-amylcinnamic aldehyde and 3,5-dimethyl-3-cyclohexene-1-carboxyaldehyde.

Examples of the phenols include methyl eugenol.

Examples of the ketones include 1-carvone, α-damascon, ionone, 4-t-pentylcyclohexanone, 3-amyl-4-acetoxytetrahydropyran, menthone, methylionone, p-t-amycyclohexanone and acetyl cedrene.

Examples of the acetals include phenylacetaldehydedimethyl acetal.

Examples of the oximes include 5-methyl-3-heptanon oxime.

Useful flavors include for example those based on aldehydes, ketones or alcohols. Examples of aldehyde flavors include: acetaldehyde (apple); benzaldehyde (cherry, almond); anisic aldehyde (licorice, anise); cinnamic aldehyde (cinnamon); citral, i.e. alpha citral (lemon, lime); neral, i.e. beta citral (lemon, lime); decanal (orange, lemon); ethyl vanillin (vanilla, cream); heliotropine, i.e. piperonal (vanilla, cream); vanillin (vanilla, cream); a-amyl cinnamaldehyde (spicy fruity flavors); butyraldehyde (butter, cheese); valeraldehyde (butter, cheese); citronellal (modifies, many types); decenal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 2-6-dimethyl-5-heptenal, i.e. Melonal TM (melon); 2,6-dimethyloctanal (green fruit); and, 2-dodecenal (citrus, mandarin). Examples of ketone flavors include: d-carvone (caraway); 1-carvone (spearmint); diacetyl (butter, cheese, "cream"); benzophenone (fruity and spicy flavors, vanilla); methyl ethyl ketone (berry fruits); maltol (berry fruits) menthone (mints), methyl amyl ketone, ethyl butyl ketone, dipropyl ketone, methyl hexyl ketone, ethyl amyl ketone (berry fruits, stone fruits); pyruvic acid (smokey, nutty flavors); acetanisole (hawthorn heliotrope); dihydrocarvone (spearmint); 2,4-dimethylacetophenone (peppermint); 1,3-diphenyl-2-propanone (almond); acetocumene (orris and basil, spicy); isojasmone (jasmine); d-isomethylionone (orris like, violet); isobutyl acetoacetate (brandy-like); zingerone (ginger); pulegone (peppermint-camphor); d-piperitone (minty); and 2-nonanone (rose and tea-like).

Examples of alcohol flavors include anisic alcohol or p-methoxybenzyl alcohol (fruity, peach); benzyl alcohol (fruity); carvacrol or 2-p-cymenol (pungent warm odor); carveol; cinnamyl alcohol (floral odor); citronellol (rose like); decanol; dihydrocarveol (spicy, peppery); tetrahydrogeraniol or 3,7-dimethyl-1-octanol (rose odor); eugenol (clove); and, p-mentha-1,8dien-7-Oλ or perillyl alcohol (floral-pine).

Some of the medicaments which can be treated include, without limitation: antiinfectives such as, for example, penicillin, terramycin, tetracycline, chlortetracycline, bacitracin, neomycin, polymyxin, gramicidin, oxytetracycline, chloramphenicol, and erythromycin, sulfonamides, including sulfacetamide, sulfamethizole, sulfisoxazole, nitrofurazone and sodium propionate; antiallergenics such as antazoline, methapyrilene, chlorpheniramine, pyrilamine and prophenpyridamine; antiinflammatories such as hydrocortisone, hydrocortisone acetate, dexamethasone, dexamethasone 21-phosphate, fluocinolone, medrysone, prednisolone, prednisolone 21-phosphate, and prednisolone acetate; decongestants such as phenylephrine, naphazoline, and tetrahydrazoline; miotics and anticholinesterases such as pilocarpine, eserine salicylate, carbachol, diisoprophyl fluorophosphate, phospholine iodide, and demecarium bromide; mydriatics such as atropine sulfate, cyclopentolate, homatropine, scopolamine, tropicamide, eucatropine, and hydroxyamphetamine; sedatives and hypnotics such as sodium pentabarbital, phenobarbital, butabarbital, amobarbital, sodium secobarbital, codeine, carbromal and sodium phenobarbital; hypotensives and vasodilators such as pentaerythritol tetranitrate, erythrityl tetranitrate and nitroglycerin; amphetamines such as diamphetamine sulfate and dextroamphetamine sulfate; hormones such as dienestrol, ethynyl estradiol, diethylstilbestrol, estradiol, methylestosterone and propeterone; cortisone; vitamins, such as vitamin E, vitamin K, vitamin $B_1$, vitamin $B_2$ and vitamin C; and tranquilizers such as reserpine, chlorpromazine hydrochloride, thipropazate hydrochloride, prednisolone, pentylene tetrazole, N-acetyl p-amino phenol, alkaloids of belladonna, atropine sulfate, hyosine hydrobromide, hyoscyamine sulfate, chlorpheniramine maleate, phenylephedrine, quinidine salts, theophylline salts, ephedrine salts, pyrilamine maleate, quaiacolglyceryl-ether-theophyllinate, etc. and sympathomimetics such as epinefrine.

Drugs can be in various forms, such as uncharged molecules, components of molecular complexes, or nonirritating, pharmacologically acceptable salts such as hydrochloride, hydrobromide, sulfate, phosphate, nitrate, borate, acetate, maleate, tartrate, salicylate, etc. For acidic drugs, salts of metals, amines, or organic cations (e.g. quaternary ammonium) can be employed. Furthermore, simple derivatives of the drugs (such as ethers, esters, amides, etc., which have desirable retention and release characteristics but which are easily hydrolyzed by body pH, enzymes, etc. can be employed. The medicament is typically coverted to liquid form for use in the invention, and such conversion can be performed prior to, during or after its incorporation in the liquid system.

Pesticides, killing/suppressing agents for various forms of bacterial, insect, animal and plant life, may also be used in performing the invention. Examples of useful pesticides include herbicides, fungicides, insecticides, nematocides, aphicides, and miticides.

Useful herbicides include S-ethyl dipropylcarbamothioate, S-propyl dipropylcarbamothioate, S-propyl butyethyl-carbamothioate, S-ethyl cyclohexylethylcarbamothioate, S-ethyl bis(2-methylpropyl)carbamothioate, S-ethyl hexahydro-1-H-azepine-1-carbothioate, S-(2,3,3-trichloro-2-propenyl)-bis(1-methylethyl)carbamothioate, 2,6-dinitro-N,N-dipropyl-4-(trifluoromethyl) benzenamine, N-butyl-N-ethyl-2,6-dinitro-4-(trifluoromethyl) benzenamine, N-(cyclopropylmethyl)-2,6-dinitro-N-propyl-4-(trifluoromethyl) benzenamine, N-ethyl N-(2-methyl-2-propenyl2,6-dinitro-4-(trifluoromethyl) benzenamine, dimethyl 2,3,5,6-tetrachloro-1,4-benzenedicarboxylate, N-(1,1-dimethylethyl)-N'-ethyl-6-methylthio)-1,3,5-triazine-2,4-diamine,2-chloro-N-(2-ethyl-6-methylphenyl)-N-(2-methoxy-1-methylethyl) acetamide, 2-chloro-N-(2,6-diethylphenyl)-N-(methoxymethyl) acetamide, the polypropylene glycol butyl ether ester of 2,4-dichlorophenoxyacetic acid and 2,6-dichlorobenzonitrile.

Suitably useful fungicides include 3a,4,7,7a-tetrahydro-2-[(trichloromethyl)thio]-1-H-isoindol-1,3(2H)-dione, 3a,4,7,7a-tetrahydro-2-[(1,1,2,2-tetrachloroethyl)thio]-1-H-isoindole-1,3(2H)-dione, 2,4,5,6-tetrachloro-1,3-benzenedicarbonitrile, and sodium methyldithiocarbamate.

Illustrations of useful insecticides include N-[[(4-chlorophenyl-)amino]carbonyl]-2,6-difluorobenzamide, 1,1'-(2,2,2-trichloroethylidene) bis(4-chlorobenzene), 2,2-dimethyl-1,3-benzodioxol-4-yl methylcarbamate, O,O-diethyl O-6-methyl-2-(1-methylethyl)-4-pyrimidinyl phosphorothioate, and O-ethyl-S-phenyl ethylphosphonodithioate.

Suitable nematocides are represented by 1,2,dibromo-3-chloropropane.

Suitable miticides are represented by propynyl sulfites, triazapentadienes, chlorinated aromatics and dinitrophenols.

A few examples of other permeants which can be used in the invention include pest repellants, including animal, bird and insect repellants exemplified by the "deets", e.g. N,N diethyl toluamide, plant growth regulators and sex lures, such as the pheromones as exemplified by 4-methyl-3-heptanone and pheromones as exemplified by 7-ethyl-5-methyl-6,8 dioxabicyclo[3.2.1]-octane.

It should be understood that any of the permeants, when they are incorporated into the liquid system, may be in the form of a precursor or derivative of the permeant which can be converted or activated to perform its permeant function at a later time, and the term permeant should therefore be understood to include such precursors or derivatives. To illustrate, the permeant may be converted or activated prior to or during the reaction herein, during use of a composition containing the reaction product or over a period of time that such a composition is in use. For example, the useful flavors include flavor acetals and flavor ketals which are converted by hydrolysis during use to corresponding alcoholic, aldehydic or ketonic flavor compounds as illustrated in U.S. Pat. No. 3,140,184 to Robbins, issued July 7, 1964 and assigned on its face to General Foods Corporation, and U.S. Pat. No. 3,857,964 to Yolles, issued Dec. 31, 1974 and assigned on its face (in part) to David E. Brook, as well as further publications listed in said patents, all of which are incorporated herein by reference.

The permeant in its pure state may for example be a solid or a liquid under standard conditions of temperature (20° C.) and pressure (1 standard atmosphere). Solid materials should be convertible to liquid form, such as by melting or dissolving in a solvent. Liquid permeants are particularly preferred for use in the invention, and especially the essential oils of olfactants; however, solid olfactants, such as the camphoraceous fragrances, are also contemplated.

One may employ any of the above-mentioned kinds of permeants and others, provided the permeant does not interfere with the reaction to the point of destroying its usefulness. The reaction employed herein is one which includes reaction of molecules of mer with other mer molecules and/or with other materials present in the liquid system. Depending upon its chemistry, the permeant may or may not participate chemically in the reaction, but it does participate in the reaction at least in the physical sense of becoming intimately distributed among or in the mer and/or mer molecules as the reaction proceeds.

Mer

According to the invention, a synthetic or natural mer, that is, a monomer, prepolymer and/or polymer (including mixtures of the foregoing), is included or distributed in a liquid system comprising a permeant (including mixtures thereof) and is reacted in the liquid system in such a manner as to significantly increase the molecular weight of the mer in the liquid system. Thus, the suitable mers are those which are capable of undergoing (with the aid of catalysts, promoters and/or other additives as required) significant increases in molecular weight in a liquid system comprising a selected permeant. The liquid system may, for example, be a permeant which is itself a liquid, or the permeant may be distributed in a liquid, such as by solution. Preferably, the mer is reacted while dissolved in the liquid system, for example in the permeant itself.

The mer can be a single material, such as a polyhydroxy polymer that complexes with the permeant or a monomer which forms a homopolymer. However, as employed herein, the singular term "mer" also refers to combinations of materials which perform the mer function. Thus, a mer may be composed of a blend of two materials that are each individually reactive, i.e. they will each react in the desired manner without the other, but the blend is useful for one or more reasons, such as contributing a particularly desired combination of physical and/or chemical properties to the resultant product. On the other hand, the mer may involve a combination of two or more dependent reactants, such as a monomer and co-monomer which react by copolymerization. Other applicable combinations include a polymer and an accompanying organic or inorganic cross-linker, coupler or coagulant.

Among the many mers which may be selected for use in the invention may be either natural or synthetic substances and include, without limitation, polyhydroxy compounds, acrylic resins, amides, and alkenyl aromatic monomers.

Examples of polyhydroxy compounds, which are preferred mers, include, without limitation, polyvinyl-pyrrolidone, polyvinyl alcohol, polyvinyl acetate, algin, agar, chitin derivatives, dextrose, cyclodextrin, cellulose and its derivatives and starch and it derivatives.

Typical of the cellulose derivatives are methyl cellulose, hydroxyethyl cellulose, hydroxypropyl cellulose, and carbomethyl cellulose. Typical starch derivatives are amylose, amylopectin, glycogen, methyl starch and hydroxyethyl starch.

Examples of monomers of the acrylic resin type include, without limitation, the hydroxy lower alkyl acrylates and hydroxy lower alkyl methacrylates such as 2-hydroxyethyl acrylate, 2-hydroxy-propyl acrylate, 3-hydroxypropyl acrylate, 2-hydroxyethyl methacrylate, 2-hydroxyethylene methacrylate, diethylene glycol monomethacrylate, 2-hydroxypropyl methacrylate, 3-hydroxy-propyl methacrylate and dipropylene glycol monomethacrylate.

Cross-linking agents which may be used with the hydroxy lower alkyl acrylates and hydroxy lower alkyl methacrylates include without limitation ethylene glycol diacrylate, propyleneglycol diacrylate, ethylene glycol dimethacrylate, 1,2-butylene dimethacrylate, 1,3-butylene dimethacrylate, 1,4-butylene dimethacrylate, and propylene glycol dimethacrylate.

A large number of other acrylates and methacrylates which are useful in the present invention are disclosed in U.S. Pat. No. 4,310,397 to Kaetsu et al. on Jan. 12, 1982 and assigned on its face to Japan Atomic Energy Research Institute, and the disclosure of polymerizerable monomers and other materials in Kaetsu et al is hereby incorporated by reference.

Examples of amides which may be used include acrylamide, n-methylacrylamide, n-isopropyl methacrylamide, n-methyl methacrylamide, n-12-hydroxyethyl acrylamide and n-(2-hydroxyethyl methacrylamide). Various cross-linkers may be used with the polyamides, such as N,N methylene-bis-acrylamide, various persulfates and others. The acylamides may also be cross-linked by irradiation with UV light.

Examples of alkenyl aromatic monomers include styrene, o-, m- and p-methylstyrene, ethyl styrene, o-chlorostyrene, vinylbenzyl chloride and p-tert-butyl styrene.

Examples of additional useful mers include 2-vinyl pyridine, 3-vinyl pyridine, 4-vinyl pyridine, vinylidene chloride acrylonitrile, vinyl acetate, divinyl benzene, butadiene, chloroprene, isoprene, itaconic acid, acrylonitrile, and acrylamides.

Examples of useful copolymers include, without limitation aromatic diisocyanates together with mono- or dialkanolamines. Typical diisocyanates include 2,6-toluenediisocyanate, 4,4-diphenyldiisocyanate, and diphenylmethane diisocyanate. Typically useful alkanolamines for copolymerization with the diisocyanates include monoethanolamine, monoisopropanolamine, and cyclohexylethanolamine.

Particularly preferred mers include the polymers described as polyvinylpyrrolidone, polyvinyl alcohol, polyvinyl acetate, vinyl amine copolymer, algin, agar, chitin, dextrans, cyclodextrins (cyclodextrin compounds, especially $\beta$-cyclodextrin), and cellulose, including the monomers and the derivatives of all of the foregoing. Other suitable mers may also be employed.

The most preferred mers at present are polyvinylpyrrolidone, alginates and chitosan, but $\beta$-cyclodextrin is also believed to be of substantial interest. Polyvinylpyrrolidone, its chemical and physical properties and its methods of manufacture and uses are described in Chapter 21 of the "Handbook of Water-Soluble Gums and Resins" by Robert L. Davidson, copyright 1980 by McGraw-Hill, Inc., which is incorporated herein by reference. Algin, its sources, manufacture, structure, other properties and uses are described in a brochure entitled "Algin/Hydrophilic Derivatives of Alginic Acid for Scientific Water Control" by Kelco Division of Merck and Co., Inc., second edition, the contents of which are incorporated herein by reference. For information on cyclodextrins, see "Celdex (Cyclodextrins)", a publication of Nihon Shokuhin Kako Co., Ltd. (13 pages), the contents of which are incorporated herein by reference. Also incorporated herein by reference is an article entitled "Entrapment of Microbial Cells in Chitosan", by K. D. Vorlop and J. Klein of the Institute of Technical Chemistry, T. U. Braunschweig, Hans Summer-Strausser 10, 330 Braunschweig, FRG, which describes chitosan, its properties and uses, as well as additional literature containing information on chitosan.

The mer currently considered best is polyvinylpyrrolidone. While the use of polyvinylpyrrolidone and its derivatives with average molecular weights in the range of about 5,000 to about 1,000,000 is contemplated, including quaternized polyvinylpyrrolidone with average molecular weights in the range of about 50,000 to about 1,000,000, best results have been obtained to date with an unmodified polyvinylpyrrolidone having an average molecular weight in the range of about 5,000 to about 200,000, and more preferably in the range of about 7,000 to about 160,000 with an average molecular weight of about 10,000 having produced the best results. This particular polymer can be readily dissolved in a wide variety of essential oils and reacted to yield products that can be readily microencapsulated in a manner further described below.

Liquid System

One of the basic characteristics of the liquid system is that it constitutes a substantially homogeneous liquid mixture of liquid, and in certain circumstances non-liquid, components. The mer and permeant, which are liquid components of this mixture, are present in forms which are substantially compatible and preferably substantially miscible with one another, most preferably constituting substantially a single phase as distinguished from an emulsion or mere mechanical dispersion. More particularly, it is preferable that the mer and permeant constitute a solution, which in the present invention includes sols and true solutions. While substantially complete solution is preferred, it is contemplated that in certain circumstances a portion including preferably the bulk or major weight portion of the mer may be dissolved to the point of disappearance into the liquid system while a minor portion thereof may be in microscopically observable colloidal "solution" or suspension.

As previously indicated, liquid permeants (e.g. essential oils) are preferred, and it is most preferred that the mer be dissolved in the permeant in the liquid system. However, for those mers and permeants which are not mutually soluble the preferred procedure involves a liquid system which is usually but not necessarily a solvent solution of the permeant. Alternatively, the permeant may be introduced into a solvent solution of the mer. Such solvent-based liquid systems are preferably based on solvent (including solvent mixtures) that is a co-solvent for mer and permeant and which may be polar or non-polar, aqueous or hydrophobic, organic or inorganic, using stirring and solubility aids as necessary.

The present invention makes possible the production of controlled release permeant concentrates which exhibit a high degree of uniformity from batch to batch and are, therefore, usable as intermediates, dependable blending components, for production of end products having lower overall concentrations of permeant. In the liquid systems used to prepare such concentrates, the permeant is present at a high weight concentration as compared to normal average concentrations in the end products. For example, in many food and beverage products, flavor essential oils are present in concentrations typically below about 1% or even below 0.1% by weight. In some polymer/perfume combinations used in products having severe deodorant requirements (e.g. animal litter), equal parts of olfactant and polymer have been used to impart a final olfactant/litter substrate ratio (solvent free basis) of about 1.25%, while the weight ratio of solvent—polymer—olfactant in the litter impregnating solutions have for example been 90:5:5. In personal perfumes, essential oil levels of about 15 to about 30% are typical. However, in preferred embodiments of the present invention, the weight percentage of permeant in the liquid system, based on the weight of permeant, mer and any solvent which may be present, is generally substantially above 5%, typically about 10% or more and most preferably about 20% or more, with about 50% or more where possible and the use of uncut essential oils being considered best. Also, it is preferred that the weight of permeant (solvent free basis) exceed the weight of mer (solvent free basis) included in the liquid system; for example permeant to mer weight ratios (solvent free basis) of about 1.05 or more, typically about 1.3 or more and frequently about 1.5 or about 2 or more are contemplated. For further discussion of principles for selecting proportions of mer and permeant, see under the heading "Reaction", below.

While the permeant and mer are essential ingredients of the liquid system, it may contain other ingredients, including components which are and are not chemically active in the reaction or final product. Included are additives which catalyze or promote polymerization and/or plasticize the resultant product, such as glycerol, carboxymethylcellulose, diethyl phthalate, sorbitol, tannic acid, persulfates, multivalent (preferably divalent) metal salts such as calcium, barium, aluminum, iron and the like, polyphosphates and other materials with similar utilities, as well as solvents, agents for adjusting or otherwise controlling the particle size of the reaction product, surfactants, and other modifiers and additives. Examples include ethanol, EDTA, nonionic surfactants, bentonite, PEG, CARBOPOLS and other modifiers and additives.

Where the final product is intended for pharmaceutical use, or for ingestion as a foodstuff, or for use in a product constituting an indirect food additive, it may be necessary or desirable to use only ingredients which are USP listed or have GRAS status, and it is an advantage of the invention that it can be readily performed with such ingredients, whereby the products will be useful in the pharmaceutical, cosmetic and food industries.

The liquid system should be pourable at specified temperatures and pressures. The herein described reaction can be conducted at temperatures of about 60° C. or less, and the liquid system should therefore constitute a pourable liquid at temperatures of about 60° C. or below, more preferably about 50° C. or below, and still more preferably at about 40° C. or below. However, those liquid systems which are pourable at about room temperature (e.g. 20° C.) are particularly preferred. The foregoing temperatures are assumed to correspond with standard atmospheric pressure or with the vapor pressure of the liquid system, whichever is greater.

Consistent with the manner in which the reaction is to be conducted, the liquid system should be formulated for stability. More specifically, the liquid system should be stable, in the face of the reaction, the foregoing temperatures and such agitation as may be necessary, against coagulation, stratifi-cation and such other forms of undesired deterioration as may seriously interfere with performance of the process.

Given the present disclosure and the working examples set forth below, persons skilled in the art will readily select appropriate permeants and mers to use in combination, based on experience or simple experiments. The identities of the materials and the relative proportions can both be selected in the foregoing manner and will be governed in part by the intended end-use of the product, with due regard as to whether it must be soluble or insoluble in a given solvent, whether it must be biologically safe, whether it will be a final product or an intermediate of another process or product, whether product life is a consideration, whether the volatility of the final product is important and to what degree, and whether the permeant includes a fragrance whose scent must be faithfully reproduced in the final product. In the last-mentioned circumstances the mer and other non-fragrance materials are preferably selected to be substantially odor-free when reacted, and preferably also when in their unreacted state.

In the preparation of the liquid system, where one or more of its components is (are) solid material(s), it may be of assistance to grind either or both of them to a fine particle size before attempting to form the above described homogeneous mixture. Thus, for example, solid mer may be ground before being dissolved in liquid permeant. Solid permeant may be ground before being mixed with liquid mer. Solid mer and permeant may both be ground to fine particle size and either premixed dry for simultaneous solution in a co-solvent or may be dissolved sequentially. Sequential solution with the mer being added to liquid permeant or permeant solution is preferred and where possible it is preferred that the mer be dissolved directly in substantially undiluted permeant. Mixing with gentle to moderate but not excessive agitation may be applied to fully dissolve the mer and permeant. Extended mixing is sometimes necessary, e.g. 24–48 hours. Gentle heating may be used when necessary. These steps set the stage for conducting the desired reaction.

Reaction

In general, the reaction contemplated by the present invention is a reaction of mer in the presence of permeant with participation of the permeant either chemically or at least in the sense of becoming intimately distributed among or in the mer and/or resultant polymer molecules as the reaction proceeds, including a significant increase in the molecular weight of the mer.

Thus, the reaction may be any chemical change which results in a significant increase in the molecular weight of the mer accompanied by a substantial reduction in the diffusion rate, volatility, flammability, toxicity or susceptibility to oxidation or other form of environmental attack, on the part of the permeant. Among the contemplated reactions are:

Polymerization—forming chain-like (including branched) macro-molecules which are the result of combining many small molecules (i.e. monomers), including homo- and co-polymerization.

Crosslinking—forming inter-connected macro-molecular chains which are the result of opening bonds (which may include opening rings) along and intermediate the ends of adjacent chains of 2 (or more) similar or dissimilar macro-molecules and connecting those bonds with one another to connect the chains together.

opening bonds (which may include opening rings) along and intermediate the ends of adjacent chains of 2 (or more) similar or dissimilar macro-molecules and connecting those bonds through the residue of a different molecule of low, medium or high molecular weight acting as a crosslinking agent.

forming ionic bonds along and intermediate the ends of adjacent chains of two or more similar or dissimilar macro-molecules; see C. F. Vorlop et al, supra, page 2; see also "ionomer resins" in Condensed Chemical Dictionary, 10th Edition, Van Nostrand Reinhold Company, New York, 1981, page 568). (include para. page 6, line 11 of existing case).

Grafting—enlarging polymeric species by adding pendant side chains to a backbone polymer.

Coupling—forming macro-molecules by end-coupling two or more large molecule (e.g. prepolymer) building blocks to each other directly or through a coupling agent in a linear or branched arrangement.

Complexing—forming or enlarging molecules by combining them with other molecules (and optionally also with themselves) in a form of association which does not involve strong chemical bonding, including for example clathrating, hydrogen bonding and/or formation of adducts, inclusion compounds or inclusion complexes in which guest molecules are incorporated in receptacles in the structures of host molecules, and forms of association based on electrostatic and ionic charges.

The significant molecular weight increase employed in the present invention is in general an increase which sufficiently provides or enhances at least one beneficial characteristic of the permeant and/or its performance in its end-use(s) to have practical application(s). Examples of such beneficial characteristics are set forth herein in the discussions of advantages and uses of the invention under the headings Summary of the Invention and Industrial Applicability. It appears that increases in the molecular weight of the mer which are very small in numerical terms can be useful for particular permeant applications, such as about one, two, three or five percent or more, ranging upwards to about fifty percent or more, based on the molecular weight of the mer prior to the reaction. Thus, the molecular weight increase may appear significant or insignificant in purely mathematical terms, but should be signficant in terms of its effect(s) on one or more characteristics of the permeant and/or its performance.

The course of the reaction and the nature of the reaction product can be controlled by making appropriate selections of proportions of mer and permeant in the liquid system. Subject to the requirement of conducting the reaction in order to substantially preserve at least one permeant function of the permeant, the concentration of mer in the liquid system can be up to about the maximum amount of mer that is soluble in the liquid system or in the permeant, but lesser amounts are preferred.

For example, relatively low mer concentrations may be preferred for certain applications, especially in the manufacture of long lasting medicaments, perfumes and similar personal care products in which an excessive amount of reacted mer might introduce excessive tackiness into the resultant reaction product, leading to an unpleasant "feel" when the reaction product is used as perfume. It has been found for instance that a concentration of about 0.1 to about 2 percent by weight of mer based on the weight of mer plus permeant is quite adequate and effective for such applications.

On the other hand, relatively high mer concentrations will be preferred for certain flavor/food/medicament applications and in olfactant applications where tack or at least higher polymer loadings are useful. In such cases, it may be found desirable to employ an amount of mer sufficient to bind to complex the majority, preferably about 60 percent or more, more preferably about 80 percent or more and still more preferably substantially all of the permeant, on a weight basis.

One convenient measure of relative proportions of reacted mer and fragrance in the reaction product in liquid, gel-type and paste-like compositions is the ratio of the weight of polymer, in grams, to the volume of the essential oil (uncut basis) in milliliters, expressed as a percentage. Useful products may for example be prepared in the range of about two or three to about eighty percent, and more preferably about eight to about thirty percent, with about fifteen percent being best for producing gels for encapsulation. By way of example, with the preferred mers described above, one can produce a variety of products ranging from longer- to very-long-lasting liquid fragrances for use as personal perfume or in aerosol air fresheners at a level of about two or three to about eight percent, liquid through gel-type products with particularly good fragrance retention properties for encapsulation within a sub-range of about eight to about thirty percent, and continuing up to exceptionally long-lasting pseudo-solid fragrances for applications such as shopping bag inserts at a level of about thirty to about eighty percent. The polymer to fragrance ratio may thus be varied to select the desired physical form and longevity of the fragrance.

Likewise, with respect to reaction products of mers and medicaments, a convenient measure of relative proportions of reacted mer and medicament in the reaction product in liquid, gel-type and paste-like compositions is the ratio of the weight of the medicament to the weight of polymer (solvent-free basis) expressed as a percentage. Useful products may for example be prepared in the range of about two or three to about eighty percent, and more preferably about eight to about thirty percent, with about fifteen percent being best for producing gels for encapsulation. By way of example, with the preferred mers described above, one can produce a variety of products ranging from longer- to very-long-lasting liquid medicaments at a level of about two or three to about eight percent, liquid through gel-type products with particularly good medicament retention properties for encapsulation within a sub-range of about eight to about thirty percent, and continuing up to exceptionally long-lasting pseudo-solid medicaments at a level of about thirty to about eighty percent. The polymer to medicament ratio may thus be varied to select the desired physical form and longevity of the medicament.

It has been found for instance that a concentration of about 0.05 to about 5% by weight of flavor based on the weight of mer plus permeant is quite adequate and effective for such applications.

On the other hand, relatively high mer concentrations will be preferred for certain flavor/food/medicament applications where tack or at least higher polymer loadings are useful. In such cases, it may be found desirable to employ an amount of mer sufficient to bind or complex the majority, preferably about 60 percent or more, more preferably about 80 percent or more and still more preferably substantially all of the permeant, on a weight basis.

One convenient measure of relative proportions of mer and flavor in the reaction product in liquid, gel-type and paste-like compositions is the ratio of the volume of the essential oil(s) (uncut basis), in milliliters, to the weight of polymer, in grams, expressed as a percentage. Useful products may for example be prepared in the range of about 0.05 or 0.5 to about 80%, and more preferably about 0.1 to about 5%, with about 0.5% being best for producing gels for edible strips. By way of example, with the preferred mers described above, one can produce a variety of products ranging from longer- to very-long- lasting liquid flavors for use as edible samplers or in drug delivery systems at a level of about 0.5 or 2 to about 10%, liquid through gel-type products with particularly good flavor retention properties for encapsulation within a sub-range of about 0.5 to about 30%, and continuing up to exceptionally long-lasting pseudo-solid flavors for applications such as shopping bag inserts at a level of about 30 to about 80%. The polymer to flavor ratio may thus be varied to select the desired physical form and longevity of the fragrance.

With particularly reactive mer combinations, the reaction may be commenced merely by combining and mixing the ingredients. However, as indicated above, initiators, catalysts, promoters and other reaction aids can be useful in practicing the invention. It has been found that the order of addition of such reaction aids can be varied. Preferably, modifiers, reaction aids and other additives are added to a mixture formed by mixing the mer thoroughly and very uniformly with the permeant, preferably for a few or even many hours. See the examples set out below. However, the afore-mentioned mixture can also be added to the catalyst, such as to a liquid system containing the catalyst in solution. If plasticizers are used, they can be added slowly with constant stirring to the afore-mentioned mixture. In certain instances, addition of plasticizer will initiate or at least promote polymerization. Generally, agitation is continued during the reaction until the desired final product is obtained. However, agitation sufficiently vigorous to emulsify the contents of the liquid system should be avoided.

With certain mers and other reactants, the reaction will proceed readily with extended stirring at room temperature. Although the process clearly is not limited to room temperature operations, it is a particular advantage of the invention that it can be performed at room temperature and at temperatures of about 60° C. or less, preferably about 50° C. or less and still more preferably about 40° or less, thereby permitting the use of temperature sensitive materials, including fragrances and other permeants which are temperature sensitive, in the product.

Depending on the characteristics of the permeant, it may be desirable to provide it with partial or complete protection from atmospheric air, such as by using a sealed reactor or mixing under vacuum or an inert atmosphere. Superatmospheric pressure or vacuum may also be employed to control particle size in those circumstances where the reaction is conducted to produce a particulate product.

Similarly, although the process is not limited to substantially neutral conditions, e.g., a pH of about 6 to about 8 or about 6.5 to about 7.5, it is an advantage of the invention that at least certain of its embodiments can be carried out within one or both of these ranges, thus making it possible to readily entrap pH sensitive materials in the resultant reaction product.

The process can be conducted in such a manner that it is compatible with biologically sensitive materials, and such materials can be incorporated into various forms of reaction product. When using biological materials it may be necessary to take precautions to protect such materials from contamination and degradation.

The progress of the reaction may be monitored in any suitable manner. For example, viscosity and/or preferably specific gravity measurements can be used. In general, other conditions remaining the same, increasing viscosity and/or specific gravity signifies increasing molecular weight of the mer in the liquid system.

The minimum acceptable proportion of mer to permeant and the minimum acceptable extent of reaction for any mer/permeant combination will be that proportion and that extent of reaction which are sufficient to cause the reaction to proceed and to cause a substantial reduction in the diffusion rate, or volatility, or flammability, or toxicity or susceptibility to oxidation or other form of environmental attack, upon the permeant. In the case of an olfactant, the said proportion and extent of reaction will be sufficient to cause a substantial reduction in the diffusion rate, or volatility or susceptibility to oxidation or other form of environmental attack, upon the permeant, or to preserve the integrity of the fragrance, including top notes thereof. Persons skilled in the art can ascertain appropriate proportions and minimum extents of reaction for the potentially useful mer/permeant combinations with the aid of simple experiments guided by the discussion which follows.

In general, the quantity of mer and extent of reaction should be sufficient to provide in the resultant reaction product an average molecular weight of about 1,000 or more. For example, some of the lower molecular weight cyclodextrins have an average molecular weight of about 1,000. More commonly, the reaction product will have an average molecular weight of about 2,000 or more. Preferred are "high" polymers, meaning macromolecules having an average molecular weight of about 5,000 or about 6,000, such as for instance cellulosic polymers. Algin has been described as a natural high polymer. More preferred are those reaction products having an average molecular weight of about 7,000 or more, for example those based on polyvinylpyrrolidone, the polyvinylpyrrolidone/permeant reaction product that is presently most preferred having an average molecular weight above about 10,000.

There is no fixed upper limit on the molecular weight range and average molecular weight of the reaction product, except that these molecular weight properties of the reaction product should be limited, in relation to the quantity and structure of the reaction product, for preserving at least one useful permeant function of the permeant and for providing acceptable levels of viscosity, permeant volatility suppression, water/oil solubility, tack (if any) and other properties that may be desired in the final product.

In general, with increasing and decreasing average molecular weight and with increasing and decreasing relative abundance of branching, ring structures and polar functional groups in the molecular structure of the reaction product, the viscosity of the reaction product respectively increases and decreases. Thus, polymeric species containing relatively high proportions of hydroxyl groups per unit average molecular weight will in general produce reaction products of higher viscosity than species with lower proportions.

Those factors which tend to produce increased viscosity are also believed to suppress permeant volatility and diffusion rate. Thus, given a polymeric specie having a predetermined degree of branching and a particular proportion of specified functional groups in its molecular structure, increasing or decreasing the average molecular weight will generally be expected to increase or decrease permeant volatility and diffusion rates.

In general, increasing the average molecular weight and the relative proportions of branching and ring structures will tend to increase the oil solubility and reduce the water solubility of the reaction product and vice versa. Contrariwise, increasing the quantity of strong polar groups, especially carboxyl and/or hydroxyl groups, tends to increase water solubility while diminishing oil solubility.

If substantial tack would be objectionable in the final product, which could be the case in a reaction product used in formulating personal perfume, then the quantity of mer and/or extent of reaction should be limited. By way of illustration, a substantial prolongation of the fragrance effects of an essential oil for personal perfume can be obtained with only about 0.75% of mer based on fragrance oil; but in the preparation of a paper coating in which tack is desirable the amount of mer can for example be about 33% based on fragrance oil.

With the aid of these explanations and information known to skilled polymer chemists, persons skilled in the art should have no difficulty selecting suitable proportions of mer and permeant and a suitable extent of reaction that will preserve the extended function of the permeant while meeting the basic requirement of sufficient proportions and sufficient reaction described above.

One may select mers, modifiers and polymerization conditions to form polymeric reaction products that are soluble or insoluble in selected solvents such as water and/or alcohols. The liquid system can be polymerized to form reaction products characterized by a variety of physical properties, including the full range of viscosities of liquids that are pourable. In certain embodiments the range of products may include those ranging in viscosity from pourable liquids through soft gels. Thus, the reaction may be terminated while the liquid system is still substantially liquid or when it has progressed to a non-shape retaining soft gel, i.e. a gel which when formed into a 2 inch unreinforced and unsupported homogenous cube, does not spread more than 20% linearly in any dimension upon standing for 8 hours at about standard atmospheric pressure at 20° C. In those instances in which relative humidity is deemed to have an influence on the performance of the sample, a relative humidity of 50% is assumed.

Industrial Applicability

The reaction products thus formed are useful as ingredients in controlled release compositions in which the permeant is used for performing a permeant function in a host medium outside the reaction product. In this connection, the permeant may constitute either the main active ingredient or an auxiliary component of the composition. In general, utilization of the reaction product in such compositions will tend to stabilize the permeant and/or enhance its effect in one or more of the ways described below and/or change the properties of the permeant in a way that makes it more useful.

For example, in many instances the formation of the reaction product will be found to reduce the differential diffusion of component parts of permeants containing multiple components. This can be useful in lengthening the shelf life of the composition by preserving the entire composition for a longer period of time.

In compositions containing permeants which do not have components which exhibit differential diffusion tendencies, incorporation of the reaction product in the composition will be found to reduce the overall diffusion rate of the permeant as compared to otherwise similar compositions containing the unreacted permeant. Here again, shelf life can be increased and absorption of the product into packaging can also be reduced. A reduction in overall diffusion rate can also impart more longevity to the composition while it is in use. An additional potential benefit is reducing wastage of the permeant, enabling its diffusion rate to be matched to the need for the permeant in the host medium into which it is released.

As permeants diffuse, they typically display a rate of diffusion which decays rapidly and then more slowly as diffusion of the permeant continues. Another of the potential benefits of the invention is that it can reduce the decay rate of the diffusion process, making possible a higher rate of diffusion during the later stages of the life of the controlled release composition.

One of the other potential stabilization benefits of incorporating these reaction products into controlled release compositions is safeguarding the permeant against unwanted chemical change. This is useful, for example, where the manufacturing process for the composition tends to adversely affect the permeant. Where the composition is a bread or cookie dough and the permeant is a flavor to be incorporated in such dough prior to baking, substituting a mer/flavor reaction product can retard chemical change in the flavor during baking. Where the composition is a packaging material and the permeant is a olfactant, formation of a mer/olfactant reaction product and incorporation of that product into the packaging material can reduce the tendency for chemical change in the olfactant during hot processing of the packaging material. Also, formation of the reaction product can slow or stop environmental attack upon the permeant by oxygen, water vapor, carbon dioxide, carbon monoxide, nitrogen and other environmental factors.

The advantage of enhancement of permeant effect follows from the manner in which formation of the reaction product affects diffusion of the permeant. Because of this stabilization, the same amount of permeant can be made more potent (available in a higher concentration) at a given time interval after initial application of the composition. This can in turn lead to the further benefit that fewer applications of the composition may be required.

When the final product is a fragrance/mer reaction product which is or has subsequently been dissolved in a typical perfume vehicle and when the resultant perfume is placed on a user's skin, it is found that the fragrance lingers for a far longer period of time than is typically experienced in the absence of the reaction product. Thus, a single application of perfume can last an extended period, i.e. substantially longer than in the case of the same perfume without reaction and worn under otherwise comparable conditions, and up to an entire day. Nevertheless, with proper selection of ingredients for the reaction product, the perfume can be readily washed off with warm soapy water whenever desired.

As indicated above, formation of the reaction product can make the permeant more useful in controlled release compositions, such as by making the permeant available in altered forms. Potential physical improvements include increased viscosity, changing normally liquid materials into solids, increasing the miscibility of permeants with other ingredients of controlled release compositions, increasing the gloss and moldability of the permeant or increasing its resilience. Potential chemical changes which can be affected by converting the permeant to a mer/permeant reaction product include reducing the reactivity or toxicity of the permeant. In other cases side effects can be controlled.

The product recovered from the above-described reaction may be ready for use, i.e. may be used in exactly the same form in which is it recovered from the reaction. An illustrative example would be performance of the reaction in a perfume. As will be illustrated below, liquid reaction products can be prepared which are useful in the formulation of personal fragrances (i.e. to be applied to the person), especially "perfumes", meaning a solution of about 15 to about 30 percent of a scented essential oil in alcohol. In the preparation of such products, the mer may be uniformly distributed and reacted in the diluted essential oil constituting the fragrance, but can be distributed (preferably dissolved) and then reacted in the uncut essential oil.

On the other hand, many of the uses of the reaction product will involve its further modification prior to use, including changes in physical form, combining the reaction product with other materials, encapsulation and application to various substrates. For example, the viscosity of liquid reaction products may be adjusted to higher or lower levels and they may be converted into gels or incorporated, such as by absorption, into solid products. Moreover liquid or gel type products may be dispersed or emulsified in compatible and incompatible liquids. Gels may be converted to solids or liquids and solids may be converted to gels or liquids by heating and/or solvent action.

The reaction products may be treated, as necessary or desireable, with appropriate coupling or cross-linking agents, which may be applied for example during or subsequent to the reaction of the present invention. For example, certain types of irradiation will cause polyvinylpyrrolidone to cross-link with itself. After a reaction product is formed between a permeant and either a soluble alginate or chitosan, the alginate or chitosan moieties in the reaction product may be coupled or cross-linked with suitable reagents. Exemplary reagents for the alginates include multivalent (preferably divalent) metal salts such as calcium, barium, aluminum, iron and the like. Exemplary reagents for chitosan are polyphosphates and others described by Vorlop et al, supra.

For example, after a biopolymer, such as alginate or chitosan, has been reacted with the permeant in a liquid system in which the biopolymer is dissolved, the resultant reaction product can then be formed into droplets in a suitable solution containing the coupling or cross-linking reagent. This may be accomplished by means as simple as dropping the permeant/mer solution dropwise into the reagent solution or by mechanically projecting droplets beneath the surface of the reagent solution. In certain circumstances it may be necessary to gently or vigorously agitate the reagent solution and even to continue agitation of that solution for a period of time after initial formation of the droplets, as illustrated in the acompanying examples. The final product can, for example, be resilient, hydrated gel-beads whose particle size may be varied by controlling the size of the droplets of permeant/mer solution initially formed in the ionic solution.

With regard to combining the reaction product with other materials, they may be incorporated into carriers which may comprise active materials or may consist or consist essentially of physiologically inert materials. Gaseous, liquid and solid diluents, as well as propellants and/or preservatives may also be mixed with the reaction products. Prior to or during their incorporation into controlled release compositions, the reaction products of the present invention may be further reacted with other materials.

Although the invention makes available useful and important products which are not encapsulated, one of the chief benefits of the invention is that it provides for the manufacture of improved encapsulated permeants, i.e. reaction products according to the invention which have been subjected to a subsequent encapsulation step, preferably microencapsulation from a liquid system as herein defined. Encapsulation, which refers to entrapping droplets or particles, each containing many molecules of a liquid, gel or solid core material, in the voids of a solidified polymer matrix or within the shells of thin-walled capsules. Examples of encapsulation techniques include spray drying, freeze drying and fluid bed coating. Dried particulate products may be prepared by spray- or freeze-drying the reaction product of the invention. Encapsulating liquid to soft gel globules of reaction product with an outer layer of solid protective and/or substantially diffusion-inhibiting material such as synthetic or natural resin may be performed during such drying step, or in a fluidized bed, or by other methods. These and other methods of encapsulation, are discussed in Shasha et al, U.S. Pat. No. 4,277,364, issued July 7, 1981 and assigned to The United States of America as represented by the Secretary of Agriculture, the Shasha patent and other source materials cited therein being incorporated herein by reference.

The Shasha et al patent also discusses certain forms of microencapsulation, including microencapsulation in a vacuum or from a liquid bath. Reaction product globules ranging in consistency from liquid to soft gel, including gel beads, made according to the invention, can be subjected to conventional liquid bath microencapsulation techniques, such as, for example, those employing ureaformaldehyde resins, gelatins and/or gums, to provide the beads or particles of reaction product with an outer shell which may be substantially impermeable or at least partly permeable. A substantial body of literature exists with respect to these liquid bath microencapsulation techniques and they will not be fully described herein. Representative teachings may be found in U.S. Pat. No. 4,606,956, to Charbonneau et al., issued on Aug. 19, 1986 and assigned on its face to Minnesota Mining and Manufacturing Company; said patent and the patents and other microencapsulation source materials described therein are incorporated herein by reference.

Microencapsulation techniques which form polymer shells in liquid baths include coacervation, interfacial polymerization and other in situ forms of generation of thin polymeric shells about cores in liquid and other forms. The most important liquid bath encapsulation techniques are:

a. Coacervation: The attraction between colloids and water of solvation is altered to such an extent that the colloid particles will tend to aggregate to form two separate and distinct liquid phases within the colloidal suspension. Both phases contain the same components with one phase (the coacervate) having a much greater concentration of colloid than the other.

The encapsulation occurs when small droplets of oil (a substantially water-immiscible liquid) are present in the colloidal suspension. As the coacervate is formed it is deposited around individual droplets. The coacervate is then hardened (gelled) by lowering the temperature below the gel point. The capsules are then dehydrated and permanently hardened.

(1) Simple coacervation: A single colloid is dispersed in water and the water of solvation is removed from around the colloid by addition of chemical compounds which have a greater affinity for water than the colloid (e.g. salts or alcohols). This causes the colloid chains to come closer together and form the coacervate.

(2) Complex coacervation: Ionic charges on the colloid chains are neutralized by mixing two colloids carrying opposite charges. See U.S. Pat. Nos. 2,800,458 and 2,800,457.

b. Interfacial polymerization: This method necessitates the use of at least a two-phase system. One of the reactants is substantially soluble in the continuous phase and substantially insoluble in the discontinuous phase (core material). The other reactant is substantially insoluble in the continuous phase and substantially soluble in the discontinuous phase. The polymerization reaction occurs at the interface between the two phases forming a polymer shell around the core material, thereby substantially completely enveloping it. This shell is substantially insoluble in both phases. In this method either phase can be an aqueous system. See. U.S. Pat. Nos. 3,577,515 and 3,575,882 and British Pat. No. 1,163,023.

For additional information and references see "Microencap-sulation, Processes and Application", J. E. Vandegaer, ed., Plenum Press, New York and London, 1974, pp. 1–37 and 89–94; W. Sliwka, Agnew. Chem. Internat. Edit., Vol. 14, No. 8, pp. 539–550, 1975; and "Capsule Technology and Microencapsulation", M. Gutcho, ed., Noyes Data Corporation, Park Ridge, N.J., 1972.

Although technology exists to form microcapsules with stronger, better defined shells, the outer shells formed with many popular liquid bath microencapsulation formulations and processes are not substantially impermeable, i.e. they offer only partial resistance to the escape of permeant. Typically, the strength and thickness of such layers are restricted for rendering them readily frangible, such as by scratching with the user's fingernail or by rupturing upon the tearing apart of a binder layer containing the capsules. In certain commercially important products rupturable capsules of this type are distributed in a rubbery or resinous film and the capsules contain a fragrance as disclosed in the above-mentioned Charbonneau patent.

Microcapsules containing the reaction product of the present invention provide particularly important advantages when utilized in an otherwise conventional manner in forming scented samplers and other advertising sampler products with or without graphic material (text or pictorial) thereon. The fact that the fragrance is entrapped in the reaction product greatly hinders the escape of the fragrance through the outer shell. Thus, where the microcapsules containing fragrance/mer reaction product are utilized in a film formed with a conventional binder in otherwise conventional scented samplers, escape of the fragrance in advance of rupture of the microcapsules is controlled to a far better extent than is now typically attained. However, when the microcapsules are fractured by rubbing the film, the resultant fragrance effect can be quite long-lasting, thus considerably extending the time period during which advertising material comprising the scented sample remains useful, and therefore increasing its potential for attracting and influencing additional potential customers for the particular fragrance. These advantages are obtained without the need for major changes in the raw materials and/or procedures for the encapsulation process.

Still another possible modification of the reaction products is their application to substrates prior to or during release of the permeant into the host medium in which it is intended to perform. The mode of application may comprise coating, including coating on the surface or absorption into the interior of the substrate. Thus porous and non-porous as well as permeable and non-permeable substrates are contemplated.

A wide range of potentially applicable substrates exist, including living and inanimate substrates. Among the living substrates are animate (animal, insect, reptile, marine or human) and plant life substrates. In the animate types, the reaction product or compositions containing the same may for example be applied to hair, skin, nails and internal parts. In plant life, the reaction products and compositions thereof may be applied to leaves, stems, fruits, vegetables, roots, seeds, and the like.

There are so many potential inanimate substrates that a complete listing herein would be impractical. A number of applicable categories of inanimate substrates include large surfaces, such as the floors and walls of buildings and the surfaces of machinery and equipment, the surfaces of particular solids, both organic and inorganic, and the surfaces and interstices of fibrous webs. Thus, gel-beads are only one of a wide variety of physical forms in which useful reaction product may be manufactured. Liquid and paste-like reaction products which may or may not be in bead form can be useful for spreading on (including into) paper, cloth and other substrates and can, for example, be employed in the manufacture of the above-mentioned scented papers, scented clothing and other products. Other examples of applicable categories of substrates are non-fibrous webs, including polymeric films and metal sheeting.

A particularly useful form of substrate is the edible web which can be used to make valuable articles when coated with reaction products (encapsulated or nonencapsulated) of a mer which includes flavor, food or medicament. Since these coated webs are intended for oral ingestion or for preparing other materials for oral ingestion, they should be composed of hygienic materials and kept sanitary. Applicable edible webs include those of paper, cardboard, polymeric films and other forms. Some examples of the applicable chemical species for making these webs include for example, natural and chemically modified starches as, for example, dextrin, dextran, amylose, and amylose cross-linked with a polyol or polypeptide; cellulose derivatives such as sodium carboxymethylcellulose, hydroxypropylmethylcellulose, hydroxyethylcellulose and the like; animal proteins such as collagen and gelatin; vegetable proteins such as corn, wheat, peanut and bean proteins; and other polysaccharides such as pectin, acacia, xanthan gum, guar gum, algin and the like; and synthetics such as polyvinylpyrrolidone, polyvinyl alcohol and the like.

A basic characteristic of these edible webs is that they will readily disintegrate and preferably also dissolve in aqueous fluids, for example water, beverages, saliva and gastro-intestinal fluids, including those of the stomach or intestines. Certain of these edible web products may also contain a binder which should preferably also readily disintegrate or preferably also dissolve in the above-described fluids. Such binder may for example be used in forming multiple layers of the edible web material, adhering protective material to the webs, and where applicable, securing to the web microcapsules containing reaction product of mer with food, flavor and/or medicament. When used, the binder should be physiologically acceptable, meaning that it is physiologically inert or therapeutic or at least free of effects which would bar any necessary government approval for its use. The coatings applied to these edible webs are preferably stable and distributed substantially uniformly over the surface of the web.

The following are a number of specific examples of end use products embodying the reaction product of the invention. These include complexes of olfactants in personal care products, other primarily odor emitting products, flavor substances, packaging materials, other shaped objects of polymeric material, candy and chewing gum, cleansing agents, pesticides, repellants, medicaments and advertising samplers containing any of the foregoing.

The olfactant complexes represent particularly preferred embodiments in that they can be formulated to provide immediate delivery of scent upon use of the personal care product containing the complex, whether in encapsulated form or not. Such a product typically releases a continuing discharge or olfactant at a rate less than that of the uncomplexed olfactant but of sufficient magnitude to favorably impact upon a wearer of the product or upon a bystander who is within two feet of the source of the olfactant and who has average olfactory activity under standard temperature and pressure. Typical of such products is faithful rendition of the olfactant including both the base note(s) and top notes when present.

Among the applicable personal care products are personal perfume, which has been discussed above, and other personal care products such as cosmetics, mouthwash, dentifrice, makeup, lotions, creams, suntan preparations, nail polish, hair products, bath foams and oils, soaps, antiperspirants, deodorants, and feminine pads, napkins and tampons. The formulation of a personal perfume has been discussed above. Many of the personal care products other than personal perfume will be formulated from a mixture of the reaction product of the invention with a physiologically acceptable carrier and such active ingredients as may be necessary or desireable. Such mixtures should be substantially uniform and stable, in normal use and/or storage, against coagulation and stratification. The reaction product may be unmodified or modified in any of the above-described manners. The physiologically acceptable carrier may be physiologically inert, or therapeutic or at least free of effects that would bar government approvals necessary for its use. Among the applicable carrier types are powders, creams, gels, lotions and other thickened or unthickened bases, including those containing oily, alcoholic and aqueous vehicles or any combination of the foregoing.

Among the other primarily odor emitting products which may constitute or include reaction products according to the invention are air/room fresheners, sachet products, floral scented sprays for silk flowers and other novelty items. The air/room fresheners may for example be the conventional vented containers containing a shaped body which is or includes reaction product according to the invention, and such reaction product may also be dispersed in a spray formulation for dispersal from a pressurized aerosol spray container. Among the applicable sachet products are the familiar porous fabric containers placed in drawers and webs of paper or other material used for covering shelves and/or lining closets and drawers.

Mer/flavor reaction products may for example be used in beverages, foods, cigarette/cigar papers/wrappers, tobacco and medicaments. Illustrative beverages include soft drinks, coffee or tea and alcoholic beverages.

While only a few examples of the many applicable foods may be mentioned, those of principal interest at present include potato chips, pretzels, popcorn, cookies, cakes, bread and other baked goods. In candy and related products mer/flavor reaction products may for example provide the flavoring for chewing gum, cough drops and breath mints.

The invention can be used to make separate mer/flavor reaction products of two different flavors which can then be separately microencapsulated and then mingled in a coating on an edible strip. One example would be peanut butter and jelly flavor.

The introduction of flavors into cigarette papers is known and the use of a mer/flavor reaction product as the flavor in this type of application should result in a much longer shelf life for the product. Similarly, flavors can be introduced into tobacco itself.

Reaction products of mer and flavor are also useful in rendering medicaments more palatable, either by incorporation mer/flavor reaction product directly in a medicament composition, such as in a menthol inhaler or by incorporating the reaction product in an edible surrounding member for the medicament. An example would be a flavored aspirin pill having an aspirin core surrounded by an edible strip impregnated with the reaction product of mer and chocolate flavor. Another example would be a flavored capsule prepared from an otherwise conventional capsule formulation into which a reaction product of mer and flavor had been introduced prior to actual formation of the capsule wall.

Another significant example is incorporation of mer/permeant reaction products in packaging materials, including such permeants as olfactants, bacteriostats and the like. For example, a mer/olfactant reaction product may be applied to a product container or its label either on surface or within a web forming the label or within a wall defining the container. The controlled release properties of the reaction product may for example perform one or more of the stabilizing functions described above.

Reaction products of mers and permeants in accordance with the invention also have application to other shaped objects of polymeric material, including both resinous and elastomeric materials. For example, mer/flavor reaction products may be applied to or incorporated within the surfaces of toys, edible book pages, baby pacifiers, baby bottle nipples, dental bridgework supports and athletic mouthpieces. Mer/olfactant reaction products can be applied to or molded into hair brushes, combs and other products.

Reaction products of mer and permeant may be formed with the main and/or auxiliary ingredients of the various cleaning agents, including detergents, sanitizing agents, solvents, waxes and the like. For example, compositions of cleansing agents may contain reaction products of mers with olfactants or sanitizing agents.

In the pharmaceutical field, the invention meets several requirements, including suitable mechanical properties and biodegradation kinetics, tissue compatibility, drug compatibility, drug permeability and ease of processing.

The invention can be used with or without a water soluble strip which holds the reaction products of mer and biologically active substances. The reaction products are, depending on the needs, fully soluble in the liquids of the body, but without swelling therein, and dissolve slowly, to provide an extended period of action for a given drug in some special dosage form.

The mechanisms by which drugs are released at a controlled rate include:

Diffusion of drug through the reaction products.

Release of trapped drug as the reaction product erodes.

Release of drug through pores in the reaction product.

Biologically active substances are bound chemically to the reaction products and enter the organism by dissolution or diffusion.

The reaction products used in the invention include two dimensional hydrophilic polymers, either homogeneous or heterogenous, physiologically inert and innocuous.

In contact with living tissue or skin whether or not borne by a soluble membrane (strip), the biologically active substances diffuse or dissolve gradually into the body.

The reaction products with or without the planar water soluble membrane, can be implanted subcutaneously or inserted in a cavity of the human body or may be applied on the surface of a wound. It is also possible to use two or more different active substances jointly.

The rate at which active substances are released depends, under otherwise constant conditions, on the ratio between the surface and the volume of the article. Small grains release the sorbed substances sooner than the larger ones.

By choosing the distribution according to a predetermined schedule, it is possible to obtain any desired change of concentration with time. The use of a water soluble membrane as a holder of the reaction product is advantageous because, when the reaction product makes direct contact with living tissue, it provides a barrier to prevent the drug from migrating outward. This aids in the penetration of the living tissue and provides a holding outer layer made of neutral non-ionogenic, inert material that is easily tolerated by the organism.

Especially formulated, the invention can be used for intramuscular application, so that the physiologically active substance, when exhausted, can be replenished by using a hypodermic needle.

The application of the mer/drug reaction product to an edible strip substrate will allow for precise drug dosage control by cutting the strip into patient definable portions.

The ingestible drug strip is especially applicable to long term repetitive dosage dispensing, i.e., a booklet of birth control medication where each strip can be imprinted with a date and/or instructions. Daily vitamin or other drugs also lend themselves to this unique form of dispensing.

The soluble nature of the strip will allow for patient selection of dosage form, edible strip or liquid; each is possible without impacting on the efficiency of the incorporated drug. These characteristics make medicaments containing the reaction products especially useful for children, and patients with oral or throat problems. This delivery form will find use among the physically disabled as well. The following are some further examples of medicament applications and benefits of the invention:

A. Pharmaceutical—Human—Ethical

1. Controlled release of topical ointments, i.e., antibiotics, steroids, hormones, anti-nausea formulas, immunologic agents.
2. Coating for bandages & surgical dressings—nonallergenic, tissue compatible, medicament inclusion.
3. Implantable matrix substrate polymer with slow release medicament inclusion i.e., birth control, insulin, anti-microbial agents.
4. Edible strip (soluble) for Rx medication—new dosage form with tremendous versatility—most current ingestible medications applicable.

B. Pharmaceuticals—Human—OTC

1. Ointments—product stability and longevity in first aid creams, burn ointments, anti-fungal/anti-bacterial products.
2. Edible strip dosage form for OTC—i.e., aspirin and related analgesics, vitamins and supplements, cold remedies.

C. Pharmaceuticals—Veterinary

1. Dermatologic shampoos with active ingredients that remain on the skin better and longer, i.e., tick and flea repellants and insecticides, anti-fungals, steroids, amino acid/proteins.
2. Edible dosage forms of products—ease of measuring and dispensing for different weights and sizes of animals, i.e., worming medicines. The process also facilitates flavoring the product for animal acceptance.
3. Controlled release of repellants and perfumes in collars, feed bowls, etc.
4. Prolonged flavor in animal toys, i.e., dog chews, rubber bones, cat toys.

D. Medical Device/Hospital Industry

1. Plastic products with anti-bacterial properties, i.e., catheters, speculums, etc.
2. Implantable devices with anti-clotting agents or other chemicals incorporated into them.
3. Hospital products with long-lasting olfactants and chemicals, i.e., bed pans molded with perfume and disinfectants.
4. Cleaning agents with high residuals of disinfectants.

Reaction products in liquid or gel form, including those which have and have not been substrate that is edible and that is intended to be eaten or at least partly ingested orally by a prospective customer. For example, the edible substrate could carry or include a reaction product of mer and food, flavor, beverage, medicament or the like which was connected with advertising material and intended to be eaten or chewed by the prospective customer. Similarly, the reaction product could be coated as a dissolvable layer upon an edible or non-edible substrate, including insoluble substrates, and could be swished about in a liquid to form a drink containing flavor or medicament which the prospective customer could swallow. Associated advertising material could be printed upon the substrate itself or upon a flyer or brochure packed in a container with the substrate, or upon a protective outer member for the substrate. It should be understood however that with respect to edible strips and advertising samplers including the same, the reaction products of the present invention are but one example of many types of controlled-release means which can be utilized for controlling release of the flavor. Thus, any presently existing or future controlled release means may be applied to these strips and samplers.

Preferably, the sampling layers containing the reaction product are applied to a "continuous" travelling web by printing or draw down techniques using a draw down bar, doctor blade or the like or any other suitable technique. Webs printed in this manner can then be cut to the appropriate size for the sampler and, if desired, combined with a suitable protective covering.

In general, a protective covering can be any device which has sufficient structural integrity to withstand normal handling of the advertising sampler during production, shipment and distribution to the prospective customer and will at least partially enclose or fully surround the portion of the sampler containing the reaction product. Partial enclosures assist in preventing premature mechanical rubbing of sample layers and particularly microcapsules while also excluding dirt. Examples of such partial enclosure include self-folds formed in substrates and a cellophane or polymeric film flap covering one or both major surfaces of a sampler substrate. A fully surrounding protective covering provides an opportunity to exclude bacteria and further reduce the opportunity for oxygen, moisture and other environmental factors to attack the reaction product. Examples of fully surrounding protective coverings include substrates confined between impermeable protective layers having full edge seals, sealed envelopes and the like.

In an advertising sampler, the substrate bearing the sample is typically connected with graphic material, including print, art work and pictures, advertising the sampled product. The appropriate connection may be direct, i.e. a connection of the graphic material and sample through the substrate which bears the sample. Examples include samplers where the sample and graphic material are on the same web or on webs which are attached to each other. On the other hand, the connection may be provided by having the graphic material and sample within one or more envelopes, such as by placing both within a common envelope. However, two-envelope systems are also applicable in which a first envelope encloses the sample while a second envelope encloses the first envelope and the graphic material.

The following examples illustrate but are not intended to limit the invention:

EXAMPLE 1

The following formulation is used for the preparation of scented samplers:
- Fragrance: 17.0%
- Polyvinylpyrrolidone: 5.6%
- Alginate (6.6% H$_2$O Solution): 19.8%
- Methyl Paraben: 0.1%
- Bentonite: 9.9%
- Glycerin: 47.6%

The fragrance, which in this case is the pure essential oil used in "Giorgio" TM perfume, is mixed and miscible with the mer, polyvinylpyrrolidone (PVP). The PVP used in this and the succeeding examples has a K value of about 15. Mixing is continued until the polymer is thoroughly dissolved in the fragrance. This is accomplished by gentle mixing for an extended period (e.g., 48 hours). All other ingredients are mixed with high shear in a separate vessel. Then, with moderate agitation, the fragrance/PVP mixture is slowly added to the other ingredients. Mixing is continued for 10–15 minutes thereafter. The resultant mixture is then applied to strips of paper and dried.

EXAMPLE 2

The following formulation can be used in forming submicron particles of reaction product for microencapsulation:
- Fragrance: 41.2%
- Ethanol: 20.6%
- Polyvinyl Alcohol: 1.0%
- Polyvinylpyrrolidone: 16.6%
- Diethylphthalate: 20.6%

The polyvinyl alcohol is dissolved in the ethanol with heat and mixing. The polyvinylpyrrolidone is added to the fragrance and stirred in a container heated in a warm water bath (50° C.) for 4 hours. Mixing is continued for an additional 24 hours at room temperature. Then, the polyvinyl alcohol solution is added to the PVP/fragrance solution and stirred for 24 hours. To the resultant mixture is added the diethyl phthalate, following which mixing is continued for an additional 48 hours. Employing gentle or vigorous stirring depending upon the particle size desired, gel-beads are formed by pouring a very thin string or stream of the resultant reaction product into a large volume of water to form a dispersion or emulsion. After recovery of the resultant gel-beads, they may be microencapsulated by any of the conventional microencapsulation processes.

EXAMPLE 3

The following formulation illustrates reduction of the water-solubility of a permeant and is suitable for production of a coffee flavor that is relatively insoluble in water:
- Flavor: 45.0%
- Polyvinylpyrrolidone: 33.0%
- Diethylphthalate: 22.0%

A mixture that has been formed by dissolving the polyvinylpyrrolidone in a mixture of essential oils having a coffee flavor with the aid of high shear mixing is stirred an additional 5 days with a low level of agitation. Then, diethyl phthalate is added to the mixture with high shear agitation. The mixture is then stirred an additional 24 hours, followed by a rest period of 24 hours without agitation. The preceding steps of stirring for 24 hours followed by a 24 hour rest period are repeated 2 additional times. The resultant water-insoluble reaction product can be diluted with solvent as needed and used as a raw material for microencapsulation or other processes. If used for production of scented samplers, glycerin or other modifiers may be added during or after polymerization.

EXAMPLE 4

The invention may be used for "encapsulation" of normal saline solution. About 1–3% of sodium alginate, grade MV, is stirred into a saline solution (0.9% NaCl) with gentle heating. The resultant reaction product solution is then added dropwise, without stirring, to a large body of 0.05–1.5 ml solution of barium chloride. The resultant liquid suspension of globules should then be stirred gently for 30–60 minutes. After the globules are recovered from the barium chloride solution and are washed with isotonic solution, they may be dried in a conventional manner to produce hydrated gel-beads.

EXAMPLE 5

To encapsulate a flavor with chitosan, (e.g. the coffee flavor of Example 3, above) first determine the pH of the flavor and then acidify as necessary to a pH of about 6 or less with acetic or hydrochloric acid. Then, dissolve the chitosan to a loading of 1–2% by weight in the flavor. The resultant solution is then added dropwise to a 1.5% solution of polyphosphate in water without stirring. After globules have formed, they should be stirred an additional 30–60 minutes to harden.

EXAMPLE 6

The following formulation is a liquid fragrance reaction product suitable for microencapsulation:
- Fragrance: 70.0%
- Polyvinylpyrrolidone: 15.0%
- Diethylphthalate: 15.0%

In this example the fragrance is the essential oil which is used in Enjeli TM perfume. The polyvinylpyrrolidone is added to the fragrance and stirred in a container heated in a warm water bath (50° C.) for 4 hours. Mixing is continued for an additional 24 hours at room temperature. To the resultant mixture is added the diethyl phthalate, following which mixing is continued for an additional 48 hours. After recovery of the resultant liquid reaction product, it may be microencapsulated by any of the conventional microencapsulation processes.

EXAMPLE 7

The following example illustrates microencapsulation of liquid reaction product that is relatively insoluble in water. In the example, the water is deionized water and all equipment is thoroughly cleaned and odor-free.

Vigorously agitate 11 grams of gum arabic and 89 grams of water to complete solution at room temperature. With similar agitation, dissolve 11 grams of 325 bloom pigskin gelatin into a solution of 0.1 gram methyl paraben in 89 grams water. After the gelatin solution has swelled for 15 minutes, place it in a water bath at 55° C. until fully liquified and then cool to 35°–40°. In the cup of a Waring blender and at 35°–40° C. mix 90 ml of the gelatin solution and 100 ml of water with slow agitation. Slowly pour into this agitated mixture at the side of the blender 120 ml of the liquid product of Example 6, above, measuring and adjusting temperature as necessary at 10 minute intervals to maintain 35°–40°. Increase agitation as necessary to obtain sufficiently small particle size for encapsulation while maintaining temperature as above described. Transfer resultant emulsion to a tank equipped with thermometer and propeller mixer and containing, at 35°–40° a mixture of 90 ml of the above-described gum arabic solution and 200 ml of water under slow agitation. Wash blender cup with an additional 100 ml of water at 35°–40° C. and also add to tank. Adjust pH to 4.90–4.95 using 13 percent (wt./vol.) acetic acid solution or 15 percent $Na_2CO_3$ (wt./vol.) solution and log temperature and pH at 15 minute intervals throughout encapsulation steps which follow. Allow batch to cool gradually and at 27° C. add above-described acetic acid solution drop-wise until pH is 4.83. When temperature has dropped to 20° C. reduce pH to 4.75 with additional acetic acid. Chill tank and contents in ice bath to 10° C. and hold for one hour. Add 5 ml glutaraldehyde, remove ice bath and allow reaction to proceed overnight. Then slowly heat batch to no more than 35°–40° and recover resultant microcapsules.

EXAMPLE 8

This example illustrates preparation of a blotter. Two 100 parts by weight of the liquid reaction product of Example 1 is added 7 parts by weight of carboxy methyl cellulose. After thorough mixing, the resultant mixture is drawn down on porous paper (e.g. Beckett Antique 2/65) at a loading of 0.019 grams of the wet coating formulation per square centimeter of paper, and the resultant coated paper is air dried.

The following example illustrates preparation of a scented paper sampler containing encapsulated fragrance. Microcapsules produced in accordance with Example 7 are introduced into a binder solution composed of 10% polyvinyl alcohol (unhydrolyzed) of medium molecular weight in water (10% solids). The capsule content of the resultant mixture is adjusted to 32% by weight of the total composition. This mixture is applied to the uncoated side of 40–120 pound (e.g. 70 pound) scent free paper which has been coated or sized on one side. The rate of application of mixture to the paper is such as to distribute 40 to 80 pounds of fragrance oil over one million (1,000,000) to two million (2,000,000) square inches of the paper which is then dried and cut into scented samplers having an area in the range of 1 to 2 square inches.

EXAMPLE 10

This example illustrates preparation of a scented printing ink. Two parts by weight of the liquid product of Example 2 are mixed with 98 parts of a commercially available ink base to form an ink having the following composition in parts by weight:

| | |
|---|---|
| Joncryl 87 - Aqueous styrenated acrylic resin dispersion (49% solids) | 19.60 |
| Jonwax 22 - Aqueous microcrystalline wax emulsion (35% solids) | 4.9 |
| Joncryl 67 - Acrylic resin, solid flakes | 5.88 |
| Aqueous Ammonia solution (28%) | 0.78 |
| Morpholine | 0.49 |
| Isopropanol | 1.96 |
| Dibutylphthalate | 0.59 |
| Ethyl glycol monoethylether | 0.59 |
| Water | 23.81 |
| Union Carbide SAG 471 Silicon Antifoamer | 0.20 |
| Carbon black pigment | 39.20 |
| Reaction Product | 2.00 |
| Total | 100.00 |

EXAMPLE 11

This example illustrates preparation of a scented printing ink. Two parts by weight of the liquid product of Example 6 are mixed with 98 parts of a commercially available ink base to form an ink having the following composition in parts by weight:

| | |
|---|---|
| Joncryl 87 - Aqueous styrenated acrylic resin dispersion (49% solids) | 44.10 |
| Jonwax 22 - Aqueous microcrystalline wax emulsion (35% solids) | 4.90 |
| Joncryl 67 - Acrylic resin, solid flakes | 6.13 |
| Aqueous Ammonia solution (28%) | 0.32 |
| Monoethanolamine | 0.49 |
| Isopropanol | 2.45 |
| Diethylaminoethanol | 0.78 |
| Water | 24.18 |
| Thalocyanine blue pigment | 14.70 |
| Reaction Product | 2.00 |
| Total | 100.00 |

EXAMPLE 12

The following formulation can be used to prepare an unencapsulated personal perfume product:

| | |
|---|---|
| Fragrance | 98.5% |
| Polyvinylpyrrolidone | 0.75% |
| Diethylphthalate | 0.75% |

In this example the fragrance is the essential oil which is used in making Enjeli ™ perfume. The polyvinylpyrrolidone is added to the fragrance and stirred in a container heated in a warm water bath (50° C.) for four hours. Mixing is continued for an additional 24 hours at room temperature. To the resultant mixture is added the diethylphthalate, following which mixing is continued for an additional 48 hours. The resultant reaction product is then cut with a conventional perfume vehicle (e.g. ethanol) to prepare a personal perfume in which the reaction product represents 22.5% of the total weight. When this perfume composition is applied to the skin it provides both satisfactory early delivery and long sustained delivery of the fragrance. Upon initial application, fragrance is delivered at a level consistent with that normally expected of a personal perfume. Even after 12 hours, fragrance is emitted at a high enough level to give a pleasing effect which is quite faithful to the original fragrance, considering the 12 hour period for which the perfume has been worn. The fragrance can however be readily removed from the skin by washing with warm soapy water.

EXAMPLE 13

This example illustrates preparation of an insect repellant soap from the following ingredients in the indicated weight percentages:
Intermediate 2020 (McLaughlin Gormley King Co.):
   15%
   N,N-diethyltoluamide (95% meta)
   MGK-264
   MGK repellant 11
   MGK repellant 326
Polyvinylpyrrolidone: 15%
Diethylphthalate: 7.5%
High fat coconut soap: 62.5%

The polyvinylpyrrolidone is mixed with the 2020 intermediate until dissolved, and the diethylphthalate is added to the resultant solution and agitate for 24 hours. After the soap is liquified by heating, it is uniformly blended with the PVP-2020-DEP solution, which blend is poured into molds and hardened. The resultant soap, after de-molding, is aged for two weeks prior to use.

Definitions

Solution—a liquid system containing intimately mixed mer and permeant in which the mer and permeant will not readily rearrange themselves into separate phases under the conditions selected for reaction of the mer in the liquid system, including for example true solutions, sols (i.e. colloidal suspensions) and combinations thereof which do not rearrange into separate phases on standing for at least 8 hours at standard temperature (20° C.) and pressure (atmospheric).

True Solution—a solution in which at least a major portion (by weight) of the mer "disappears" into the permeant, i.e. is no longer separately visible with the naked eye or under a microscope of 1200 power, and is neither detectable by Coulter Counter nor separable from the liquid system by centrifugation.

Predominately True Solution—a true solution in which at least about 75% (by weight) of the mer "disappears" (as defined under "True Solution").

Complete Solution—a true solution in which substantially all of the mer "disappears" (as defined under "True Solution").

Liquid System—a system which will pour and flow when the temperature of the system is about 60° C. or less. If pouring and flowing are affected by the pressure conditions within the system, the above indicated temperature of 60° will be assumed to correspond with standard atmospheric pressure. A liquid system may be composed of materials which, individually, will and will not pour and flow under the indicated conditions.

Homogeneous (as applied to Liquid System)—a liquid system wherein the liquids, solids (if any) and gases (if any) present in the system are distributed throughout the system in a substantially uniform manner.

Encapsulate/encapsulation—the act of fact of entrapment of small particles comprising clusters of molecules of a core material (including droplets, tiny gel beads or solid particles) by solidification of a surrounding polymeric medium, including micro-encapsulation.

Micro-encapsulation—forming substantially complete surrounding shells around tiny particles (including droplets, gel beads and solids) by coacervation, in situ polymerization or other form of thin shell formation in a multiple phase liquid system in which microcapsules are recovered from the system.

Olfactant (olfactory agent)—an agent useful for imposing desired olfactory impressions on humans, animals and insects. Included among olfactants are fragrances, substances which emit a scent generally accepted as having a pleasing or attractive quality; odor masking materials which may or may not create a strong or distinctive olfactory impression of their own, but are useful in masking the presence of disagreeable odors; and odoriferous materials, which may be pungent or disagreeable but are nevertheless useful, such as for instance for warning or cautionary purposes.

Perfume—a composition comprising about 15% to about 30% by weight of the essential oil of a fragrance dissolved in a volatile alcoholic carrier which may also contain water and other additives.

While the invention has been described and disclosed in certain terms and has been illustrated by disclosure of certain embodiments or modifications, persons skilled in the art who have acquainted themselves with the invention will appreciate that it is not necessarily limited by such terms nor to the specific embodiments and modifications disclosed herein. Thus, a wide variety of alternatives, suggested by the teachings herein, can be practiced without departing from the spirit of the invention, and rights to such alternatives are particularly reserved, especially those which fall within the scope of the appended claims.

I claim:

1. A method of modifying a permeant comprising forming a liquid system consisting of a polymer-containing member selected from the group consisting of polyvinylpyrrolidone or a derivative thereof, a combination of polyvinylpyrrolidone or a derivate thereof and a plasticizer, and a combination of polyvinylpyrrolidone, a solvent and a plasticizer, reacting the polymer-containing member in the presence of the permeant for significantly increasing the effective molecular weight of the polymer therein under conditions which substantially preserve at least one useful permeant function of the permeant, continuing the reaction under such conditions to a sufficient extent for substantially reducing the diffusion rate, volatility, flammability, toxicity or susceptibility to oxidation or other form of environmental attack upon the permeant and recovering a reaction product having a consistency ranging from a liquid to a non-self-supporting soft gel, from which the permeant may escape for performing its permeant function in or on a host medium outside the reaction product.

2. The method of claim 1 wherein the mer includes polyvinylpyrrolidone having a molecular weight in the range of about 5,000 to about 200,000.

3. The method of claim 1 wherein the mer includes polyvinylpyrrolidone having a molecular weight in the range of about 7,000 to about 160,000.

4. The method of claim 1 wherein said plasticizer is diethylphthalate.

5. The method of claim 1 wherein said permeant is an olfactant.

6. The method of claim 1 wherein said permeant is a flavorant.

7. The product of claim 1.

8. The product of claim 7 wherein the mer includes polyvinylpyrrolidone having a molecular weight in the range of about 5,000 to about 200,000.

9. The product of claim 7 wherein the mer includes polyvinylpyrrolidone having a molecular weight in the range of about 7,000 to about 160,000.

10. The product of claim 7 wherein said plasticizer is diethylphthalate.

11. The product of claim 7 wherein said permeant is an olfactant.

12. The product of claim 7 wherein said permeant is a flavorant.

* * * * *